United States Patent [19]
Imre et al.

[11] 4,289,881
[45] Sep. 15, 1981

[54] PROCESS FOR THE PREPARATION OF 1,4-DIAZABICYCLO-(2,2,2)-OCTANE

[75] Inventors: Laszlo Imre, Leverkusen; Walter Horstmann, Bergisch Gladbach; Hans-Gerhard Leopold, Cologne, all of Fed. Rep. of Germany

[73] Assignee: Bayer Aktiengesellschaft, Leverkusen, Fed. Rep. of Germany

[21] Appl. No.: 84,928

[22] Filed: Oct. 15, 1979

[30] Foreign Application Priority Data

Oct. 27, 1978 [DE] Fed. Rep. of Germany ....... 2846813

[51] Int. Cl.³ ............................................ C07D 295/02
[52] U.S. Cl. ................................................. 544/352
[58] Field of Search .......................................... 544/352

[56] References Cited

U.S. PATENT DOCUMENTS

| | | | |
|---|---|---|---|
| 2,985,658 | 5/1961 | Krause | 544/352 |
| 3,166,558 | 1/1965 | Masaoli | 544/352 |
| 3,956,329 | 5/1976 | Murakami et al. | 544/352 |

OTHER PUBLICATIONS

Ohhashi et al., Chem. Abs. 84, 180284m.

*Primary Examiner*—Mark L. Berch
*Attorney, Agent, or Firm*—Sprung, Felfe, Horn, Lynch & Kramer

[57] ABSTRACT

A process for the preparation of 1,4-diazobicyclo-(2,2,2)-octane by contacting piperazine with a catalyst at an elevated temperature, the catalyst containing silicon dioxide.

10 Claims, No Drawings

PROCESS FOR THE PREPARATION OF 1,4-DIAZABICYCLO-(2,2,2)-OCTANE

The invention relates to a process for the preparation of 1,4-diazabicyclo-(2,2,2)-octane from piperazine compounds.

To prepare 1,4-diazabicyclo-(2,2,2)-octane from N-(β-aminoethyl)-piperazine, the following are used as catalysts: γ-aluminum oxide, according to U.S. Pat. No. 3,157,657, 10% strength tungsten oxide on aluminum oxide, according to U.S. Pat. No. 3,056,788, aluminum silicate, according to U.S. Pat. No. 2,985,658, and synthetic zeolites, according to Japan Kokai No. 7,558,096. The following are also used as catalysts in the preparation of 1,4-diazabicyclo-(2,2,2)-octane from N-(β-hydroxyethyl)-piperazine or from N,N'-bis-(β-hydroxyethyl)-piperazine: metal phosphates, according to U.S. Pat. No.3,297,701, metals on oxidised supports, according to U.S. Pat. No. 3,285,920, aluminum silicates, according to U.S. Pat. No. 3,166,558, aluminum oxide or aluminum silicate, according to Japan Kokai No. 7,511,797, bentonite, according to DE-OS (German Published Specification) No. 1,445,578, and aluminum silicates, molybdenum silicates, magnesium silicates and zeolites, according to DE-OS (German Published Specification) No. 1,445,418.

All these methods are very expensive. The reactions proceed very unspecifically on the catalysts described, with the formation of numerous by-products, the separation of which involves considerable expense. Such by-products are for example piperazine or ethanolamine which are obtained in high concentration according to the described process. The ratio of piperazine to 1,4-diazabicyclo-(2,2,2)-octane was 1:3 to 1:1 (cf.: Japan Kokai 7558096, U.S. Pat. No. 3,297,701). 1,4-diazabicyclo-(2,2,2)-octane is not able to be isolated economically from such mixtures. 1,4-Diazabicyclo-(2,2,2)-octane is obtained with insufficient purity.

A process has been found for the preparation of 1,4-diazabicyclo-(2,2,2)-octane by catalytic reaction of piperazine compounds at elevated temperature, which process is characterised in that piperazine compounds of the formula

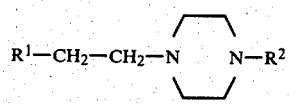

wherein
R¹ denotes the hydroxyl group or the amino group and
R² represents hydrogen or the radical

—A—R³ wherein
A denotes a straight-chain or branched hydrocarbon, e.g. a divalent alkylene, alkenylene, cycloalkylene, cycloalkenylene radical, especially of 1 to 6 C-atoms and
R³ denotes the hydroxyl group or the amino group, are reacted in the presence of a catalyst containing silicon dioxide, in the temperature range from 200° to 500° C.

The process according to the invention can be illustrated using the following equation as an example:

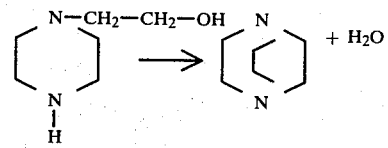

Straight-chain or branched hydrocarbon radicals (A) which may preferably be mentioned are alkylene radicals having up to 6 carbon atoms. Alkylene radicals having 2 to 4 carbon atoms are particularly preferred. The following radicals may be mentioned as examples: methylene, ethylene, propylene, iso-propylene, butylene, iso-butylene, tert.-butylene, pentylene, iso-pentylene, hexylene and iso-hexylene.

Specific piperazine compounds which may be mentioned are: N-(β-hydroxylethyl)-piperazine, N,N'-bis-(β-hydroxyethyl)-piperazine, N-(β-hydroxyethyl)-N'-(β-aminoethyl)-piperazine, N-(β-aminoethyl)-piperazine, N,N'-bis-(β-aminoethyl)-piperazine, N-(β-hydroxypropyl)-N'-(β-aminoethyl)-piperazine, N-(β-hydroxypropyl)-N'-(β-hydroxyethyl)-piperazine, N-(β-aminoethyl)-N'-(β-hydroxy-propyl)-piperazine, N-(β-aminoethyl)-N'-(γ-aminopropyl)-piperazine, N-(β-hydroxyethyl)-N'-(β-hydroxyethyl)-N'-(γ-aminopropyl)-piperazine, N-(β-hydroxyethyl)-N'-(β-methyl-γ-aminopropyl)-piperazine, N-(β-aminoethyl)-N'-(β-methyl-γ-aminopropyl)-piperazine and N-(β-aminoethyl)-N'-(δ-amino)-(butyl)-piperazine.

Particularly preferred piperazine compounds which may be mentioned are: N-(β-aminoethyl)-piperazine, N,N'-bis-(β-aminoethyl)-piperazine, N-(β-hydroxyethyl)-piperazine and N,N'-bis-(β-hydroxyethyl)-piperazine.

The preparation of the piperazine compounds for the process according to the invention is in itself known (Ber.dtsch.Ges. 59,2423 (1926); Am.Soc. 68,1296(1946): U.S. Pat. No. 3,089,876; U.S. Pat. No. 3,031,452.

They can be prepared, for example, by reaction of β-bromoethylphthalimide with piperazine and subsequent hydrolysis with hydrochloric acid.

Catalysts which contain silicon dioxide can be used for the process according to the invention. The content of free SiO₂, after calcining at 800° C., is at least 97% by weight. The proportions of other oxides can be, for example: up to 3% by weight of MgO, CaO, Fe₂O₃, K₂O and Na₂O. Catalysts of this type can also contain traces of NaCl and/or NaSO₄. For example, the silicic acid products prepared in accordance with the process described in German Offenlegungsschrift (German Published Specification) No. 1,767,754 the disclosure of which is hereby integrated herein by reference, are suitable as catalysts for the process according to the invention. According to this Offenlegungsschrift (Published Specification), porous, abrasion-resistant, bead-shaped products containing predominantly silicic acid are obtained by suspending solids in an aqueous stable silicic acid sol having a BET specific surface area of 150 to 400 m²/g, mixing the resulting suspension with an aqueous slurry of hydrated magnesium oxide in amounts of 0.1–3% by weight (relative to the anhydrous granules), dispersing this gellable mixture to give drops of the desired size, gelling the drops in a water-immiscible liquid and separating the granules from the liquid, drying and calcining them, whereby a filler, containing silicic acid and having a BET specific surface area of 20 to 200 m²/g, is suspended in the silicic acid sol in amounts of 20 to 60% by weight (relative to the dry granules) and clay minerals from the group comprising kaolinite, montmorillonite and attapulgite are suspended in the silicic acid sol in amounts of 5 to 30% by weight, the resulting suspension is gelled by addition of the hydrated, finely-divided magnesium oxide and dispersion of the suspension in a water-immiscible medium to give bead-shaped granules and the granules are then dried and hardened for at least 10 minutes at temperatures of 500° to 1,000° C. On continuous exposure to heat up to about 750° C., the chemical and physical properties of these silicic acid products do not change (Erdöl und Kohle, 23, 648 to 651 (1970)).

Further possible processes for the preparation of the catalyst containing silicon dioxide are summarised in Ullmanns Encyklopädie der technischen Chemie (Ullmann's Encyclopaedia of Industrial Chemistry), 3rd edition, volume 15, pages 712–732 (1964). The usual starting materials are silicic acids (silica sol, silica gel and kieselguhr) which form grains when introduced dropwise, stirred or sprayed into water-immiscible liquids, for example into paraffin oil. They are dried at 100° C. and are obtained in the anhydrous form after calcining at 800°–1,000° C.

Catalysts containing silicon dioxide which have a BET internal surface area of more than 30 m²/g (Brunnauer, Emmet and Teller, Journal of American Chemical Society, 60, 309 (1938)) are generally employed for the process according to the invention. For example, catalysts having a BET internal surface area of 50 to 800 m²/g, preferably of 80 to 500 m²/g, can be employed.

The catalyst can be in various forms, for example as a powder, in the form of coarse grains or in the form of spheres, extrudates, pellets or cylinders, and it can be in a fixed bed or, for better heat removal, in a fluidized bed or another moving catalyst bed. For working in a fluidized bed, sphere-shaped catalyst particles, for example, having a diameter of 0.01 to 2 mm are preferred. In a fixed bed, any form of catalyst particles having a particle size of generally about 0.2 to 20 mm can be used. Extrudates having a length of 4 to 18 mm or spheres having a diameter of 0.4 to 10 mm are also preferred.

Pure silicon dioxide is particularly preferably used as the catalyst for the process according to the invention, that is characterised as follows: BET internal surface area 80 to 500 m²/g, sphere-shaped particles having a diameter of 0.4 to 4 mm and arrangement of the catalyst in a fixed bed or in a fluidized bed.

If the catalyst loses activity through separation of impurities, the initial activity can immediately be produced again by burning off in the presence of air at elevated temperature, for example at 400° to 750° C.

The process according to the invention is carried out in the gas phase. Within the range for working in the gas phase, pressure, temperature, composition of the gas mixture and flow rate can be varied within wide limits.

The process according to the invention can be carried out at normal pressure, reduced pressure or elevated pressure. The process according to the invention is generally carried out in the pressure range from 0.01 to 100 bars. The process is preferably carried out at pressures of 0.03 to 30 bars.

The reaction temperatures for the process according to the invention are generally in the temperature range from 200° to 500° C. The process is preferably carried out in the temperature range from 240° to 350° C.

The piperazine compounds for the process according to the invention can be employed in the pure form or in a mixture with other gases. The piperazine compounds for the process according to the invention are preferably employed in a mixture with an inert gas. Inert gases for the process according to the invention are noble gases, nitrogen, steam and/or hydrogen and/or ammonia. Preferred inert gases are nitrogen, steam and ammonia.

For the process according to the invention, piperazine compounds are preferably employed in a mixture with the inert gases in a concentration of 2 to 50% by volume, particularly preferably of 5 to 25% by volume, in the gas phase.

The flow rate of the gas mixture in the reactor can be varied within wide limits. For the process according to the invention, the flow rate is preferably adjusted so as to give contact times in the reaction space of 0.01 to 50 seconds, particularly preferably of 1 to 10 seconds, calculated for the catalyst charge at a given reaction temperature.

According to the different possibilities for arranging the catalyst, the reactor can be in various forms. If the process is carried out with a fixed bed catalyst, the catalyst can, for example, be firmly fixed in one or more reaction tubes (tube reactor). The reaction tubes can consist of metal, a ceramic mixture or glass or quartz. Metal tubes, for example made of steel, are preferably used. If the catalyst is used in the form of a fluidized bed, a fluidized bed reactor of customary design (Verfahrenstechnik katalytischer Reaktionen in Katalysatoren, Tenside und Mineralöladditive (Process technology of catalytic reactions in catalysts, surface-active agents and mineral oil additives), G. Thieme Verlag Stuttgart (1978) is appropriately used. The starting materials can be introduced into the reactor and heated in various ways. For example, the piperazine compounds can be directly mixed with nitrogen in the varporizer and the starting mixture thus obtained can initially be preheated in a heat exchanger to, for example, 240° to 300° C., and then inclined into the reactor where it is further heated, if appropriate, up to the reaction temperature. However, the reactants can also be heated separately and introduced separately into the reactor.

It is particularly preferred, for the process according to the invention, to carry out the reaction in such a way that only a partial reaction takes place. Conversions up to 2 to 80%, preferably from 5 to 50%, are preferred in this case. Particularly high selectivities are achieved with this procedure.

The gases leaving the reactor generally consist of 1,4-diazabicyclo-(2,2,2)-octane, unreacted piperazine compounds and the inert gases which may be present therein. By-products which can be obtained are higher molecular compounds which can very easily be separated from the 1,4-diazabicyclo-(2,2,2)-octane prepared according to the invention. In this manner, 1,4-diazabicyclo-(2,2,2)-octane is obtained in high purity by the process according to the invention.

The 1,4-diazabicyclo-(2,2,2)-octane can be separated from the reaction mixture in accordance with known processes (for example fractional distillation, sublimation or recrystallisation). For example, the vapours separated from the catalysts can be condensed by cooling and the condensate can be fractionally distilled at normal pressure. The vapours can be cooled, for example, in the temperature range from −50° to +50° C., appropriately at about 0° C. By fractional distillation, an essentially 1,4-diazabicyclo-(2,2,2)-octane is then obtained in the boiling range from about 160° to 180° C. and at a pressure of about 1 bar, which product can be converted into a highly pure product by further distillation and/or sublimation.

The 1,4-diazabicyclo-(2,2,2)-octane can also be purified according to U.S. Pat. No. 2,937,176 by triturating the product with a liquid, low-boiling, aliphatic hydrocarbon, such as, for example, n-pentane, and cooling the mixture, whereupon the 1,4-diazobicyclo-(2,2,2)-octane precipitates in high purity.

The still impure 1,4-diazabicyclo-(2,2,2)-octane can also be recrystallised from ethyl acetate.

In a preferred embodiment of the process according to the invention, the procedure is as follows: the piperazine compound is vaporized in a vaporizer at about 240° C. and mixed with steam so as to produce a gas mixture having the composition of 5 to 25% by volume of the piperazine compound and 75 to 95% by volume of steam. If appropriate, the gas mixture thus obtained is heated in a preheater to the reaction temperature of 240° to 350° C. and passed, at about 1 bar, over the catalyst consisting of silicon dioxide. The flow rate is adjusted so as to give contact times of between 1 and 10 seconds. The gas mixture leaving the reactor is cooled down to 0° C. and the condensate is worked up by distillation and recrystallization. The residual gas remaining after the separation of the 1,4-diazabicyclo-(2,2,2)-octane formed and the unreacted starting material is fed back into the reaction. The proportion of starting material which has been consumed is thereby appropriately replaced.

The process according to the invention can be carried out discontinuously and continuously.

1,4-Diazabicyclo-(2,2,2)-octane can be prepared in a simple manner with high selectivity and large yields in accordance with the process according to the invention.

The reaction of the process according to the invention is surprising because 1,4-diazabicyclo-(2,2,2)-octane can be prepared in a simple manner on inexpensive catalysts with very good purity and is frequently suitable for immediate further processing in industry.

1,4-Diazabicyclo-(2,2,2)-octane can be used in the preparation of polyurethanes (Ullmanns Enzyklopädie der Technischen Chemie (Ullmann's Encyclopaedia of Industrial Chemistry), volume 7, page 386, 4th edition, (1974)).

For the purpose of the following examples, the terms conversion and selectivity are defined as follows:

% conversion = $\frac{\text{mols of starting compound reacted}}{\text{mols of starting compound employed}} \cdot 100$ % selectivity = $\frac{\text{mols of 1,4-diazabicyclo-(2,2,2)-octane formed}}{\text{mols of starting compound reacted}} \cdot 100$

EXAMPLE 1

14.0 cm³ of silicon dioxide, as the catalyst, are packed into an electrically heated, vertically arranged reaction tube which has a length of 50 cm and a diameter of 2.40 cm and is made of glass. The catalyst consists of pure SiO₂ grains. The specific surface area is 110 m²/g. The grains are in the form of spheres with an abrasion-resistant surface. The grain size distribution is in the range from 0.4 to 2 mm diameter. The length of the catalyst section is 3 cm. This section has a homogeneous temperature which is kept at 275° C. The reaction proceeds in this temperature zone.

7 g of N-(β-hydroxyethyl)-piperazine are metered every hour, at 240° C., into a vaporizing vessel having a volume of about 100 cm³ and mixed with 5 N l of nitrogen at a total pressure of 1 bar. This corresponds to a starting composition of 19.7% by volume of N-(β-hydroxyethyl)-piperazine and 80.3% of nitrogen. The gas mixture thus obtained is passed over the catalyst. A throughput of 3.46 cm³/second and a contact time of 4.1 seconds are calculated from the numerical values indicated. The gas stream vapours leaving the reactor are condensed at 0° C. by cooling.

In order to obtain the diazabicyclooctane from the reaction mixture, the total condensed phase is initially fractionally distilled at 1 bar. A fraction containing a high proportion of diazabicyclooctane is obtained as the crude product in the boiling range from 160° to 180° C. This fraction is then recrystallised from ethyl acetate. In the course of 20 hours, 14.6 g of diazabicyclooctane in the pure form are obtained under the reaction conditions indicated. The conversion and the selectivity were determined by gas chromatography in accordance with the internal standard method. The column used was 10% CARBOWAX 20 M on CHROMOSORB W. Apart from the unreacted N-(β-hydroxyethyl)-piperazine, virtually the only product which can be established from the chromatogram is 1,4-diazabicyclo-(2,2,2)-octane. The selectivity was 57.6% for a conversion of 26.2%. The unreacted N-(β-hydroxyethyl)-piperazine can be fed back for further reaction.

EXAMPLES 2 TO 10

The procedure of Example 1 was followed but other silica gel products, having a SiO₂ content of at least 99.5% in the calcined state, were used as catalysts. The gas composition, contact time, temperature, catalyst surface area and the conversions and selectivities obtained at 1 bar are shown in each case in Table 1 below.

TABLE 1

| Example No. | Silica gel surface area (m²/g) | Temperature (°C.) | Contact time (seconds) | Gas composition | | | Conversion (%) | Selectivity (%) |
|---|---|---|---|---|---|---|---|---|
| | | | | HEP | N₂ | H₂O (% by volume) | | |
| 2 | 480 | 285 | 1.7 | 19.7 | 80.3 | — | 33.8 | 54.7 |
| 3 | 620 | 315 | 0.8 | 12.1 | — | 87.9 | 25.3 | 58.0 |
| 4 | 180 | 320 | 4.3 | 24.0 | — | 76.0 | 22.8 | 54.0 |
| 5 | 440 | 260 | 10.2 | 19.7 | 80.3 | — | 30.8 | 47.6 |
| 6 | 110 | 290 | 2.1 | 19.7 | 80.3 | — | 21.8 | 63.9 |
| 7 | 110 | 280 | 2.3 | 10.9 | 89.1 | — | 22.6 | 69.3 |
| 8 | 270 | 275 | 1.2 | 5.3 | — | 94.7 | 14.4 | 71.2 |
| 9 | 90 | 350 | 0.5 | 9.4 | 45.3 | 45.3 | 27.4 | 48.1 |

TABLE 1 -continued

| Example No. | Silica gel surface area ($m^2/g$) | Temperature (°C.) | Contact time (seconds) | Gas composition HEP | Gas composition $N_2$ | $H_2O$ (% by volume) | Conversion (%) | Selectivity (%) |
|---|---|---|---|---|---|---|---|---|
| 10 | 270 | 240 | 12.0 | 27.8 | 71.2 | — | 16.4 | 42.5 |

HEP = N-(β-hydroxyethyl)-piperazine

EXAMPLE 11

A silica gel packing having a length of 5 cm is introduced into a pressure tube which has a length of 32 cm and a diameter of 1.8 cm and is made of V4A steel. The $SiO_2$ content is above 99.5%. The specific surface area is about 500 $cm^2/g$ and the grain size is 1.5 to 3 mm. Of a gas mixture of the following composition: 19.7% by volume of N-(β-hydroxyethyl)-piperazine and 80.3% by volume of $N_2$, is passed over this catalyst at 8 bars, at a temperature of 250° C. and at a rate of 11 liters/hour. Under these conditions, a selectivity of 59.2% is achieved for a conversion of 27.8%.

EXAMPLE 12

The procedure of Example 11 is followed but 7 g of N,N'-bis-(β-hydroxyethyl)-piperazine, dissolved in 15 g of water, is metered every hour into the vaporizing vessel. The resulting gas mixture is then passed over the catalyst at 65 mbars and 310° C. The gas mixture leaving the reactor is condensed by cooling and analysed by gas chromatography. A selectivity of 44.7% is achieved, that is to say that 44.7% of the N,N'-bis-(β-hydroxyethyl)-piperazine reacted has been converted to diazabicyclooctane. The conversion is 32.3%.

EXAMPLE 13

The process is carried out in the same apparatus as in Example 1 but a gas stream consisting of 19.7% by volume of N-(β-aminoethyl)-piperazine and 80.3% by volume of nitrogen is produced and passed over the catalyst. Under the same conditions as in Example 1, a conversion of 23.0% and a selectivity of 32.7% is achieved.

EXAMPLE 14

(comparative example)

The same procedure was followed as in example 1, but a commercially available zeolite 4 A was used as catalyst, 1,4-diazobicyclo-(2,2,2)-octane was obtained having a selectivity of 28.7% for a conversion of 33.6%. Also a large amount of piperazine was detected. The ratio of piperazine to 1,4-diazabicyclo-(2,2,2)-octane was 1:2.7.

EXAMPLE 15

(comparative example)

The same procedure was followed as in example 1, but a commercially available aluminum silicate having the composition 87.3% $SiO_2$, 12.4% $Al_2O_3$, 0.25 $Na_2O$ and a BET surface of 290 $m^2/g$ was used as catalyst. The selectivity achieved was 34.2% for a conversion of 38.5%. Furthermore, the ratio of piperazine to 1,4-diazabicyclo-(2,2,2)-octane was 1:2.3.

What is claimed is:

1. A process for the preparation of 1,4-diazabicyclo-(2,2,2)-octane which comprises contacting a piperazine compound of the formula

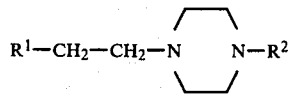

wherein
$R^1$ denotes the hydroxyl group or the amino group and
$R^2$ represents hydrogen or the radical $$-A-R^3$$

wherein
A denotes a straight-chain or branched hydrocarbon radical and
$R^3$ denotes the hydroxyl group or the amino group, at a temperature in the range from 200° to 500° C. with a catalyst containing at least 97 percent by weight free silicon dioxide.

2. A process according to claim 1 wherein said catalyst consists essentially of said silicon dioxide.

3. A process according to claim 1 wherein said catalyst comprises pure silicon dioxide.

4. A process according to claim 1 wherein the silicon dioxide of said catalyst has a BET internal surface area of more than 30 square meters per gram.

5. A process according to claim 1 wherein the process is carried at a pressure in the range of from 0.01 to 100 bars.

6. A process according to claim 5 wherein the contact time of the piperazine compound with the catalyst is 0.01 to 50 seconds.

7. A process according to claim 1 wherein the piperazine compound is employed in admixture with an inert gas.

8. A process according to claim 7 wherein said inert gas is steam and/or nitrogen and/or ammonia.

9. A process according to claim 1 wherein said piperazine compound is N-(β-hydroxyethyl)-piperazine, N,N'-bis-(β-hydroxyethyl)-piperazine, N-(β-hydroxyethyl)-N'-(β-aminoethyl)-piperazine, N-(β-aminoethyl)-piperazine, N,N'-bis-(β-aminoethyl)-piperazine, N-(β-hydroxypropyl)-N'-(β-aminoethyl)-piperazine, N-(β-hydroxypropyl-N'-(β-hydroxyethyl)-piperazine, N-(β-aminoethyl)-N'-(β-hydroxy-propyl)-piperazine, N-(β-aminoethyl)-N'-(γ-aminopropyl)-piperazine, N-(β-hydroxyethyl)-N'-(γ-aminopropyl)-piperazine, N-(β-hydroxyethyl)-N'-(β-methyl-γ-aminopropyl)-piperazine, N-(β-aminoethyl)-N'-(β-methyl-γ-aminopropyl)-piperazine or N-(β-aminoethyl)-N'-(δ-aminobutyl)-piperazine.

10. A process according to claim 2 wherein said catalyst is in admixture with another oxide selected from the group consisting of MgO, CaO, $Fe_2O_3$, $K_2O$ and $Na_2O$.

* * * * *